(12) United States Patent
Cheng (10) Patent No.: US 11,096,598 B2
(45) Date of Patent: Aug. 24, 2021

(54) SYSTEM AND METHOD FOR NON-INVASIVE MONITORING OF CENTRAL VENOUS PRESSURE

(71) Applicant: Mespere Lifesciences Inc., Waterloo (CA)

(72) Inventor: Xuefeng Cheng, Waterloo (CA)

(73) Assignee: Mespere Lifesciences Inc., Waterloo (CA)

( * ) Notice: Subject to any disclaimer, the term of this patent is extended or adjusted under 35 U.S.C. 154(b) by 204 days.

(21) Appl. No.: 15/288,275

(22) Filed: Oct. 7, 2016

(65) Prior Publication Data

US 2017/0100044 A1 Apr. 13, 2017

Related U.S. Application Data

(60) Provisional application No. 62/238,957, filed on Oct. 8, 2015.

(51) Int. Cl.
*A61B 5/021* (2006.01)
*A61B 5/00* (2006.01)
(Continued)

(52) U.S. Cl.
CPC ........ *A61B 5/02141* (2013.01); *A61B 5/0059* (2013.01); *A61B 5/02152* (2013.01); *A61B 5/02156* (2013.01); *A61B 5/6822* (2013.01); *A61B 5/704* (2013.01); *A61B 2562/043* (2013.01); *A61G 13/04* (2013.01); *A61H 2201/5069* (2013.01); *A61H 2230/30* (2013.01); *A61H 2230/305* (2013.01)

(58) Field of Classification Search
CPC ... A61B 5/021; A61B 5/02141; A61B 5/6822; A61B 2562/0233; A61B 2562/043; A61B 5/1455; A61G 13/04; A47C 19/045; A61H 2201/5069; A61H 2230/30; A61H 2230/305
See application file for complete search history.

(56) References Cited

U.S. PATENT DOCUMENTS 4,321,930 A 3/1982 Jobsis et al.
5,069,214 A 12/1991 Samaras et al.
(Continued)

FOREIGN PATENT DOCUMENTS

CA 2439161 A1 10/2002
CA 2494030 2/2004
(Continued)

OTHER PUBLICATIONS

Seth, R., Magner, P., Matzinger, F. and Van Walraven, C. (2002), How Far is the Sternal Angle from the Mid-righ Atrium?. Journal of General Internal Medicine, 17: 861-865. doi: 10.1046/j. 1525-1497. 2002.20101.x.
(Continued)

*Primary Examiner* — Christian Jang
*Assistant Examiner* — Karen E Toth
(74) *Attorney, Agent, or Firm* — Gowling WLG (Canada) LLP; Susan Tandan (57) ABSTRACT

A system for measuring central venous pressure is provided comprising a device for measuring jugular venous pressure in communication with a patient inclination controller via a processing unit.

6 Claims, 5 Drawing Sheets

(51) Int. Cl.
*A61B 5/0215* (2006.01)
*A61G 13/04* (2006.01)

(56) References Cited

U.S. PATENT DOCUMENTS

| | | | |
|---|---|---|---|
| 5,101,825 | A | 4/1992 | Gravenstein et al. |
| 5,269,310 | A | 12/1993 | Jones et al. |
| 5,788,641 | A | 8/1998 | Policastro et al. |
| 6,078,833 | A | 6/2000 | Hueber et al. |
| 6,151,518 | A | 11/2000 | Hayashi |
| 6,334,065 | B1 | 12/2001 | Al-Ali et al. |
| 6,496,711 | B1 | 12/2002 | Athan et al. |
| 6,587,703 | B2 | 6/2003 | Cheng |
| 6,801,648 | B2 | 10/2004 | Cheng et al. |
| 7,610,638 | B2 | 11/2009 | Kramer et al. |
| 7,725,187 | B1 | 5/2010 | Nabutovsky et al. |
| 7,738,935 | B1 | 6/2010 | Turcott |
| 8,417,306 | B2 | 4/2013 | Cheng |
| 8,463,348 | B2 | 6/2013 | Cheng |
| 8,788,005 | B1 | 7/2014 | Cheng |
| 8,918,153 | B2 | 12/2014 | Cheng |
| 2006/0137577 | A1* | 6/2006 | Chang ............... A61B 5/00 108/7 |
| 2006/0189872 | A1 | 8/2006 | Arnold |
| 2006/0224053 | A1 | 10/2006 | Black et al. |
| 2006/0253007 | A1 | 11/2006 | Cheng |
| 2007/0167783 | A1 | 11/2007 | Vikomerson |
| 2009/0326352 | A1* | 12/2009 | Cheng ............... A61B 5/021 600/324 |
| 2010/0198027 | A1 | 8/2010 | Dixon |
| 2010/0222658 | A1 | 9/2010 | Cheng |
| 2010/0275376 | A1* | 11/2010 | Benzo ............... A61G 7/0155/618 |
| 2012/0209095 | A1 | 8/2012 | Huiku |

FOREIGN PATENT DOCUMENTS

| | | |
|---|---|---|
| CA | 2815643 | 7/2012 |
| EP | 2120689 | 11/2009 |
| JP | 11-244268 | 9/1999 |
| JP | 2003-532107 | 10/2003 |
| JP | 2005-533609 | 11/2005 |
| WO | 2001/084107 | 11/2001 |
| WO | 2004/010844 | 2/2004 |
| WO | 2006/097910 | 9/2006 |
| WO | 2006/124696 | 11/2006 |
| WO | 2007/012197 | 2/2007 |
| WO | 2007/097702 | 8/2007 |
| WO | 2008/098353 | 8/2008 |
| WO | 2008/134813 A1 | 11/2008 |

OTHER PUBLICATIONS

Garg et al., "Jugular Venous Pulse: An Appraisal", Journal, Indian Academy of Clinical Medicine, vol. 1, No. 3, Oct.-Dec. 2000.

O'Rourke, R.A. and Others, General Examination of the Patient, Hurst's, The Heart, Eight Edition, pp. 238-242.

Conway "Clinical Assessment of Cardiac Output", Eur. Heart J. 11, 148-150 (1990).

Linton et al., "Advances in Non-invasive Cardiac Output Monitoring", Annals of Cardiac Anaesthesia, 2002, vol. 5, p. 141-148.

Conway, "Thermodilution Method for Measuring Cardiac Output", Europ. Heart J. 11 (Suppl 1), 17-20, 1990.

Lund-Johansen, "The Dye Dilution Method for Measurement of Cardiac Output", Europ. Heart J. 11 (Suppl1), 6-12 (1990)).

deLeeuw and Birkenhager ("Some comments of the usefulness of measuring cardiac output by dye dilution", Europ. Heart J. 11 (Supple 1), 13-16 (1990)).

Keinanen, "Continuous Measurement of Cardiac Output by the Fick Principle: Clinical Validation in Intensive Care", Critical Care Med 20(3), 360-365 (1992).

Doi et al., "Frequently Repeated Fick Cardiac Output Measurements During Anesthesia", J. Clin. Monit. 6, 107-112 (1990).

Botero, et al., "Measurement of cardiac output before and after cardiopulmonary bypass: Comparison among aortic transit-time ultrasound, thermodilution, and nonivasive partial CO2 rebreathing", J. Cardiothoracic Vasc. Anesth. 18 (5) 563-572 (2004).

Nilsson et al. "Lack of Agreement Between Thermodilution and CO2-rebreathing Cardiac Output" Acta Anaesthesiol Scan 2001; 45:680.

Schmidlin et al., "Transoesophageal Echocardiography in Cardiac and Vascular Surgery: Implications and Observer Variability", Brit. J. Anaesth. 86(4), 497-505 (2001).

Manning et al. "Validity and Reliability of Diastolic Pulse Contour Analysis (Windkessel model) in Humans", Hypertension. 2002 May 2002; 39(5):963-968.

Rauch et al., "Pulse Contour Analysis Versus Thermodilution in Cardiac Surgery", Acta Anaesthesiol Scand 2002:46:424.

Linton et al., "A comparison of Cardiac Output Derived from the Arterial Pressure Wave Against Thermodilution in Cardiac Surgery Patients" BR J Anaesth 2001; 86:486.

Jansen et al., "A Comparison of Cardiac Output Derived from the Arterial Pressure Wave Against Thermodilution in Cardiac Surgery Patients" BR J Anaesth 2001; 87:212.

Jansen et al. "An Adequate Strategy for the Thermodilution Technique in Patients During Mechanical Ventilation", Intensive Care Med 1990: 16-422.

http://depts.washington.edu/physdx/neck/tech2.html.

Coquhoun et al. Non-invasive estimation of jugular venous oxygen saturation: a comparison between near infrared spectroscopy and transcutaneous venous oximetry. Journal of Clinical Monitoring and Computing (2012) 26:91-98.

Xing et al.—"New Method for Non-Invasive Quantification of Central Venous Pressure by Ultrasound", ahajournals.org Jun. 19, 2020.

* cited by examiner

SYSTEM AND METHOD FOR NON-INVASIVE MONITORING OF CENTRAL VENOUS PRESSURE

FIELD OF THE INVENTION

The present invention generally relates to the measurement of central venous pressure (CVP), and a system useful for CVP determination.

BACKGROUND OF THE INVENTION

To date, the standard for measuring central venous pressure (CVP) is through the use of invasive CVP catheters.

U.S. Pat. No. 8,417,306 introduces a non-invasive optical method of measuring CVP which involves detecting the height of jugular venous pulse (JVP) on the neck of a patient relative to the superior vena cava of the right heart, e.g. using a reference such as the phlebostatic axis or sternal angle. In using this method, the patient may require adjustment in order to have an inclination angle that permits JVP is detection on the patient's neck, and to ensure that the top of the NP falls within the range of the probe used for detection. For example, a fluid-loaded patient having a high CVP may need to sit at a more inclined angle, while a "dry" patient having a lower CVP may need to lie at a more declined angle or supine. This manual adjustment process can make the CVP measurement troublesome. It may take some time to suitably adjust a patient, and is generally most readily conducted in a clinical setting.

However, there is a need to monitor CVP of chronic patients outside of the clinical setting, for example, to monitor congestive heart failure patients in long term care centres or at home. Thus, it would be desirable to develop a CVP measurement device appropriate for such use.

SUMMARY OF THE INVENTION

A novel device has now been developed which readily permits adjustment of the inclination angle of a patient when CVP is being measured.

Thus, in one aspect, a system for measuring central venous pressure in a patient is provided comprising a device for measuring jugular venous pressure in communication with a patient inclination angle controller via a processing device.

This and other aspects of the invention are described in the following detailed description by reference to the following figures.

DETAILED DESCRIPTION OF THE INVENTION

Figure 1:
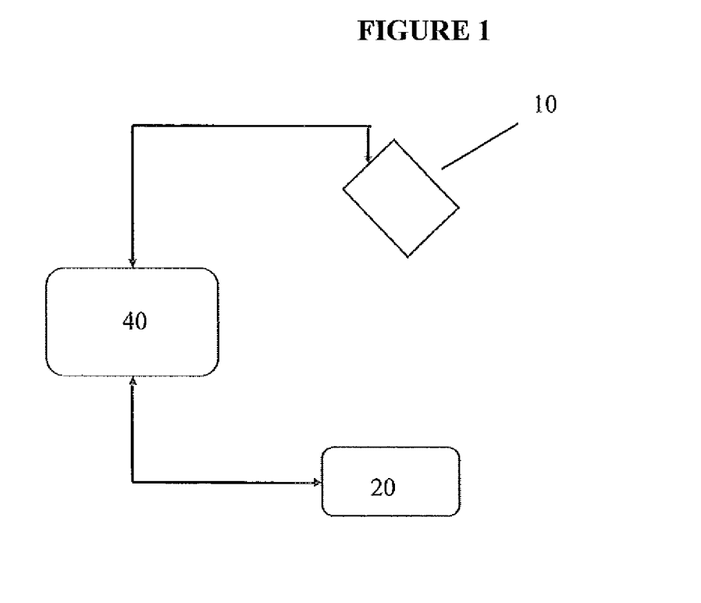
FIG. 1 generally illustrates a system comprising a device for measuring jugular venous pressure and a patient inclination controller.
Figure 2:
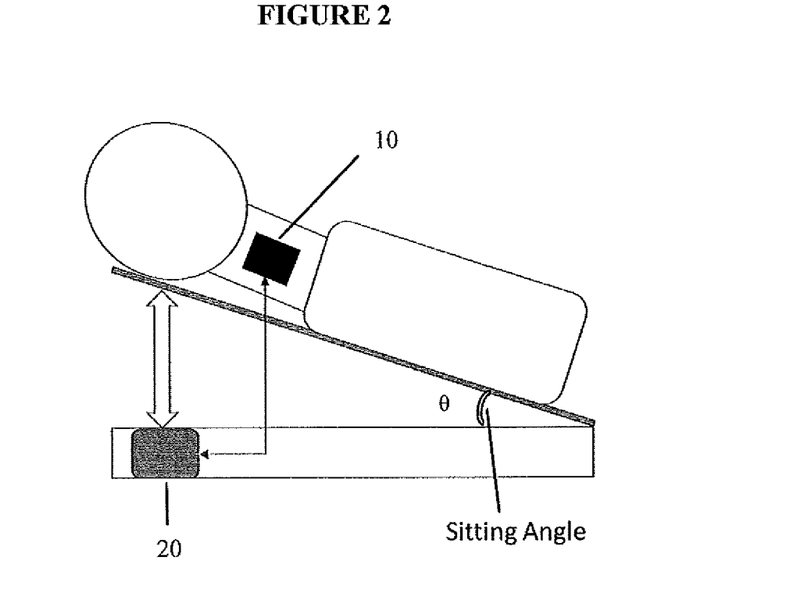
FIG. 2 illustrates the system of FIG. 1 being used on a patient.

In one aspect, a system for measuring central venous pressure as shown in FIG. 1 is provided comprising a device for measuring jugular venous pressure 10 in communication with a patient inclination controller 20 via a processing unit 40. The system may be utilized as shown in FIG. 2.

The device for measuring jugular venous pressure 10 may be any suitable device for this purpose, including optical devices, ultrasound devices and pressure sensors.

Figure 3:
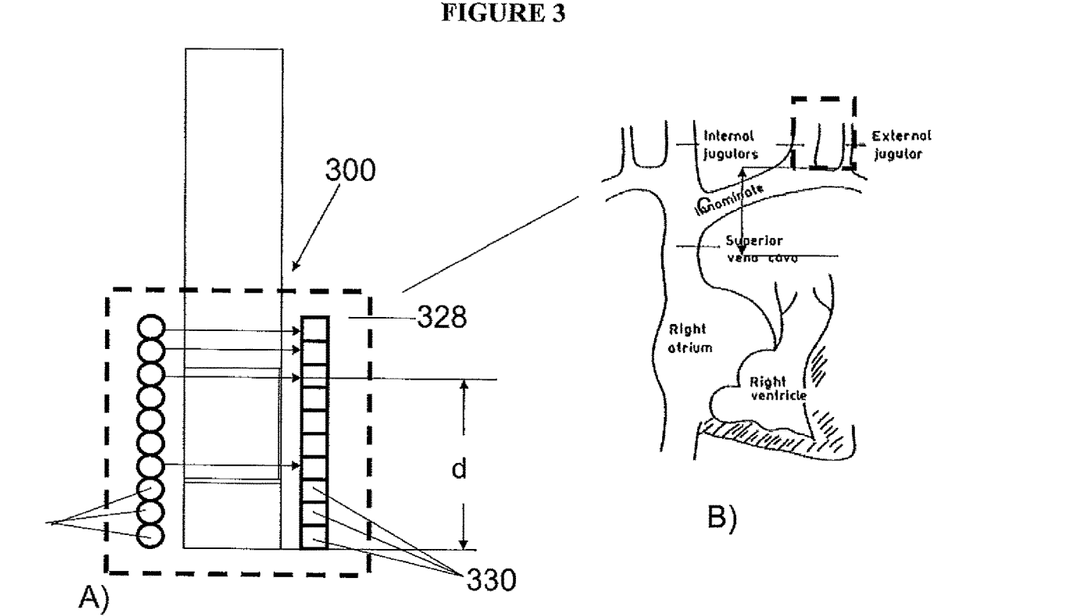
FIG. 3 illustrates (A) an embodiment of an optical device for use in a system of FIG. 1, and (B) the physiological location of the internal and external jugular veins.

In one embodiment, an optical device for measuring jugular venous pressure as previously described in PCT Publication No. WO 2014/124520 (the relevant contents of which are incorporated herein by reference) may be used in the present system. The device 300, as shown in FIG. 3, includes a series of light sources 320 located adjacent to one another along a length appropriate to measure the blood level in a jugular vein, such as the internal or external jugular vein. The length may generally be about 1.5 to 10 cm. Each light source 320 emits light at a wavelength of from 400 nm to 1000 nm and is associated with a corresponding photodetector 330 suitable to detect reflected or transmitted light from its corresponding light source 320. The device 300 additionally includes a patch probe 328 that functions as the interface between the light sources (320) and photodetectors (330) and is adapted for placement on a patient at a site in the vicinity of a jugular vein, e.g. on the patient's neck. The probe 328 may incorporate the light sources 320 and photodetectors 330 directly, or may instead incorporate light transmitting optical fibres and light receiving optical fibres connected to the light sources and photodetectors, respectively, or may include a combination of these, e.g. light sources and light receiving optical fibres, or light-transmitting optical fibres and photodetectors.

In use, the device 300 is placed on the patient at an appropriate site in which a terminal light source in the series is lined up with a reference such as the sternal angle or phlebostatic axis. The light from each light source is detected by its corresponding photodetector. The output signal (e.g. current/voltage) of each photodetector is monitored (or transmitted to a signal processing device for translation to an alternate form of output such as a visual waveform output which is monitored) to determine whether there is an output or not. The highest position (M) along the vein to yield an output, e.g. a waveform, is then determined based on the output from each photodetector in the sequence. The highest position (M) refers to the highest position of blood within the vein since the height of blood within a jugular vein directly reflects central venous pressure. The mean central venous pressure (P) may then be calculated as known in the art. For example, the mean central venous pressure (P) is calculated as follows: $P = M \cdot \sin\theta$, wherein M is the distance from the phlebostatic axis to the highest position that yields a waveform, and the symbol, $\theta$, is the inclined angle of the patient's upper body relative to the horizontal position. Central venous pressure may also be calculated using the sternal angle as the reference point. In this case, P=5+M·sin θ, wherein the addition of 5 to M represents the distance from the sternal angle to the right atrium.

Figure 4:
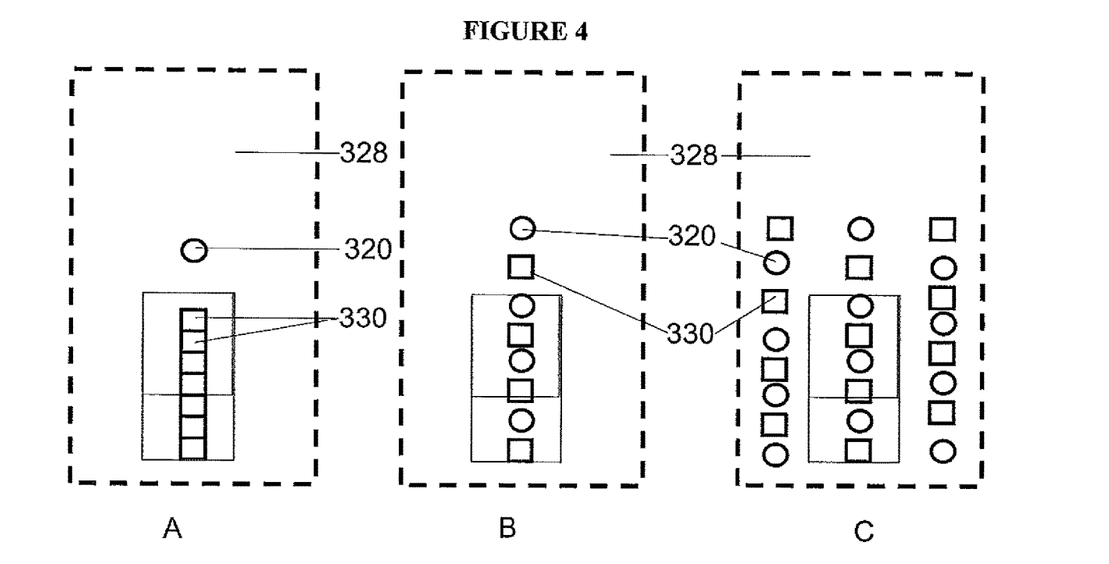
FIG. 4 illustrates additional embodiments (A, B and C) of optical devices for use in a system of FIG. 1.

FIG. 4 illustrates other embodiments of the device 300 that may also be useful to measure central venous pressure as described above. Each embodiment includes a different configuration of the light source(s) and photodetectors. For example, FIG. 4A illustrates a device including a single light source and an array of adjacent photodetectors that may be used to obtain an output, e.g. a waveform, sequentially along a vein to determine the highest position (M). FIG. 4B illustrates a device including sequential light source-detector pairs in an alternating configuration (light source-detector, light source-detector, etc.) for placement along a vein as shown. FIG. 4C illustrates a device similar to that of FIG. 4B including multiple rows of alternating light source-detector pairs. The photodetectors in each embodiment may be situated along a length of about 1.5 to 10 cm.

The optical JVP devices may include any suitable light source such as a laser diode (e.g. RLT7605G, 760 nm, 5 mW, sm, 9.0 mmh, or RLT8510MG, 850 nm, 10 mW, sm, 5.6 mm), a light emitting diode (LED) or a broadband light source emitting a selected wavelength. In an embodiment, the light source is adapted to emit light in two or more wavelengths, e.g. by association with a frequency oscillator. The light source is powered by an appropriate power supply such as a 12V DC power supply. As known in the art, light from the light source may be directed or focussed using optical lenses into transmitting optical fibre bundles which may also be used to receive reflected/transmitted light for conveyance to a photodetector. The photodetector, which translates received reflected/transmitted light into a recordable output such as current or voltage, may be any suitable photodetector such as a silicon photo diode (e.g. Hamamatsu S8553). The light source(s) and photodetectors (or optical fibre bundles) may be set directly in a patch probe, as described above, for placement at a distinct site on the patient to measure JVP. The patch probe may be made out of any material suitable to support the electronic/optical components it houses, e.g. light source, photodetector, optical fibres or mirrors, and which is compatible for placement on the skin, e.g. medical rubber, and may be modified by addition of suitable adhesives, straps, Velcro and the like to maintain its position in use.

Figure 5:
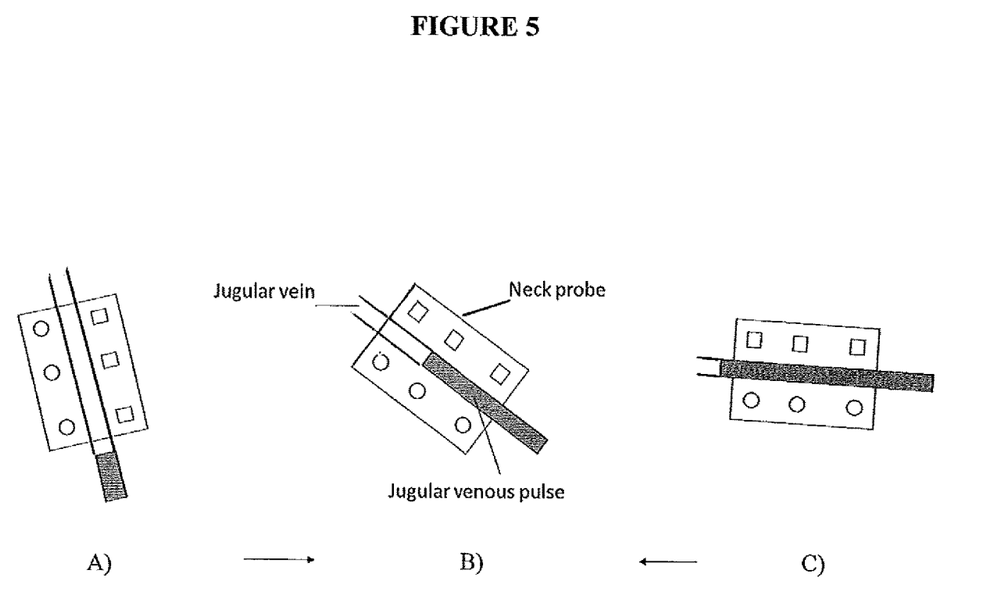
FIG. 5 illustrates use of an optical device for measuring jugular venous pressure on a patient, including an example of its use when patient inclination is too high (A), when patient inclination is appropriate (B), and when patient inclination is too low (C)

The patient inclination controller 20 functions to adjust the sitting angle of a patient to enable central venous pressure to be determined in instances in which the sitting angle is such that central venous pressure cannot be determined. For example, in use, the JVP device 10 is placed on a patient's neck in the vicinity of a jugular vein as shown in FIG. 5. If the patient's sitting angle is too high, the JVP device will detect no signal at any photodetector and, thus, will be unable to determine the highest position (M) along the vein to yield an output, preventing determination of central venous pressure (FIG. 5A). This information is communicated to the inclination controller 20, as described in more detail below, which in turn will cause the patient to be more declined (e.g. decrease the patient's sitting angle) such that the highest position along the vein to yield an output can be determined (FIG. 5B). If the patient's sitting angle is too low, the JVP device will detect a signal at each photodetector, and thus, will also be unable to determine the highest position (M) along the vein to yield an output, preventing the determination of central venous pressure (FIG. 5C). This information will be communicated to the inclination controller 20, which in turn will cause the patient to become more inclined such that the highest position along the vein to yield an output can be determined (FIG. 5B).

Figure 6:
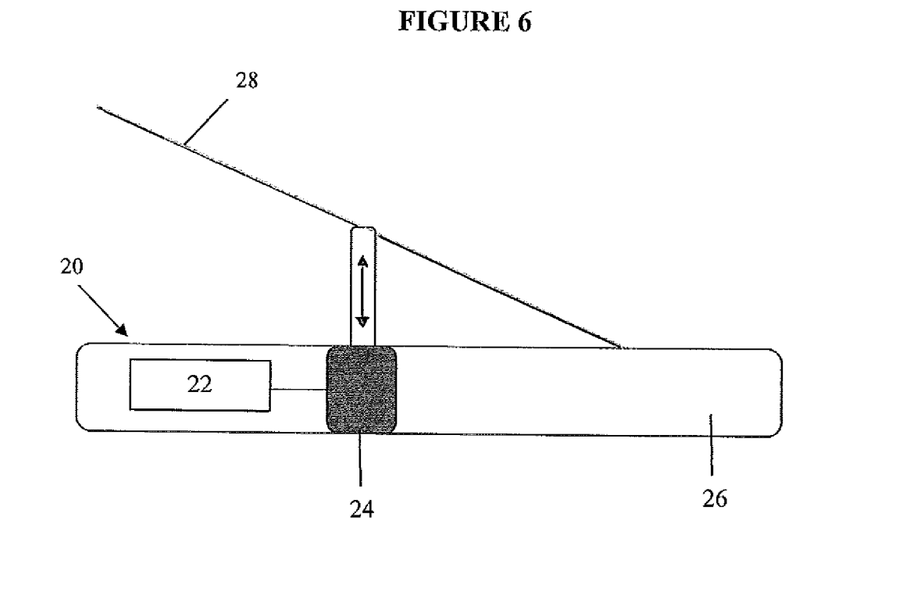
FIG. 6 illustrates an inclination controller for use in the system of FIG. 1.

As shown in FIG. 6, the patient inclination controller 20 comprises a control circuit (e.g. Thomson DCG controls) 22 which controls a linear actuator 24 (e.g. Thomson Max Jac® linear actuator). The control circuit 22 and linear actuator 24 are housed in a base 26. A back support 28 is moveably connected to the base 26 and is movable between a base position in which the back support 28 lies adjacent to the base 26 and a multitude of inclined positions from the base by the linear actuator 24. The back support 28 is sufficient to support the weight of a patient and may be used with an inclinable chair or bed, or may form part of an inclinable chair or bed, such that the angle of a patient using such chair or bed may be adjusted as described. The control circuit 22 controls the up and down movement of the linear actuator 24 to adjust the inclined position of the back support 28. The control circuit 22 is in communication with the processing unit 40, which processes signal information from the JVP device 10, and then activates the linear actuator 24 accordingly to adjust the back support 28 up or down as required to adjust patient inclination such that the JVP device 10 is able to ascertain M (the highest position along the jugular vein to give an output reading) for the determination of central venous pressure.

Figure 7:
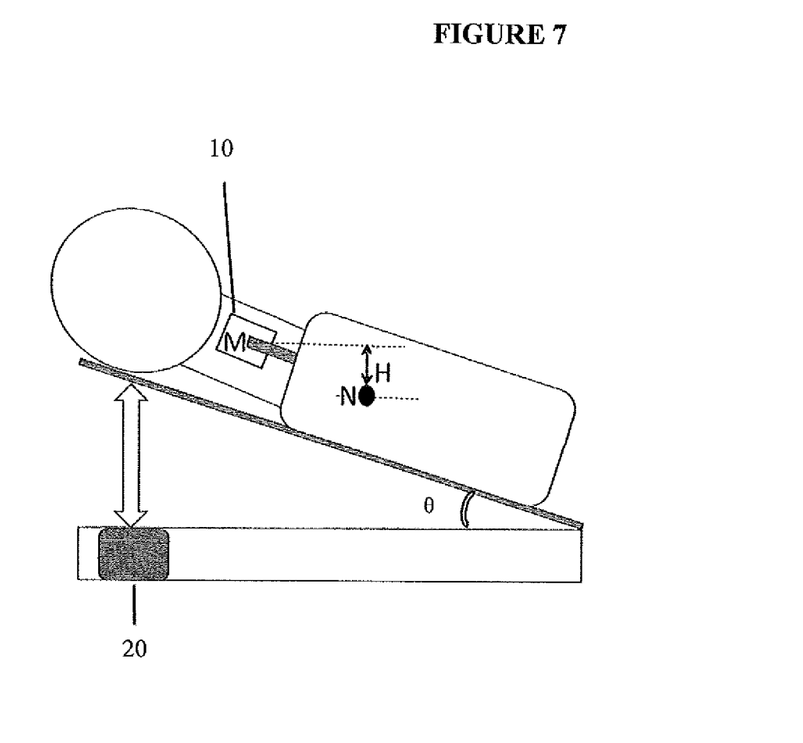
FIG. 7 illustrates use of an inclination controller in a system according to FIG. 1.

FIG. 7 illustrates the determination of central venous pressure using the present system. As shown, M is the highest position along the vein to yield an output (e.g. the top of the jugular venous pulse as measured by the JVP device). N is the position of the phlebostatic axis (PA) reference of the patient. H is the vertical height difference between M and N (conventionally, H is measured in centimetres using a ruler, electronic or other height measurement tool). CVP equals H cm $H_2O$ (since the density of blood is very similar to that of water). However, as one of skill in the art will appreciate, CVP can be converted from cm $H_2O$, to another preferred unit of measurement.

In one embodiment, the patient's initial position is supine, and the inclination controller 20 activates inclination of the patient gradually until the JVP device is able to detect to the highest position along the vein to yield an output from which CVP is then calculated. In another embodiment, the patient's initial position is sitting upright, and the inclination controller 22 activates declination of the patient gradually until the JVP device is able to detect the highest position along the vein to yield an output from which CVP can be calculated.

The device for measuring JVP 10 and patient inclination controller 20, are connected, either directly or wirelessly, to a processing unit 40. The signal processing unit 40 includes a signal processing device that is operable to receive signals from the JVP device provided by the photodetector(s) (e.g. the time varying current/voltage signals) and translate these signals into a visual output, such as a waveform, numerical or other readout. Thus, the signal processing device is operable to digitize the output provided by the JVP device into a recordable output for presenting on a display. The signal processing device may include a microprocessor (e.g. digital signal processor, Texas Instruments) or digital acquisition board to digitize the signal (e.g. current/voltage), and a display unit, such as a monitor, which is in communication with or connected to the microprocessor, and functions to display the signal as an output. The signal processing device may be separate from the display unit, and in communication with an external display unit for presenting the output of the signal processing device thereon. For convenience, the display unit, e.g. monitor, may be portable, e.g. a handheld unit, and/or battery operated. Such a handheld unit may be connected by a cable or wirelessly to the JVP device. The system may further include a docking station for docking and charging a handheld monitor, or a docking station for the JVP device, optionally including a unit adapted to calibrate the probe. The signal processing device may further comprise an algorithm processing module. The processing unit 40 is also in communication with the patient inclination controller 20, to provide information thereto, as above described, which permits the circuit controller 22 to appropriately activate the linear actuator 24 and adjust inclination of the back support 28 and thereby adjust patient inclination.

Figure 8:
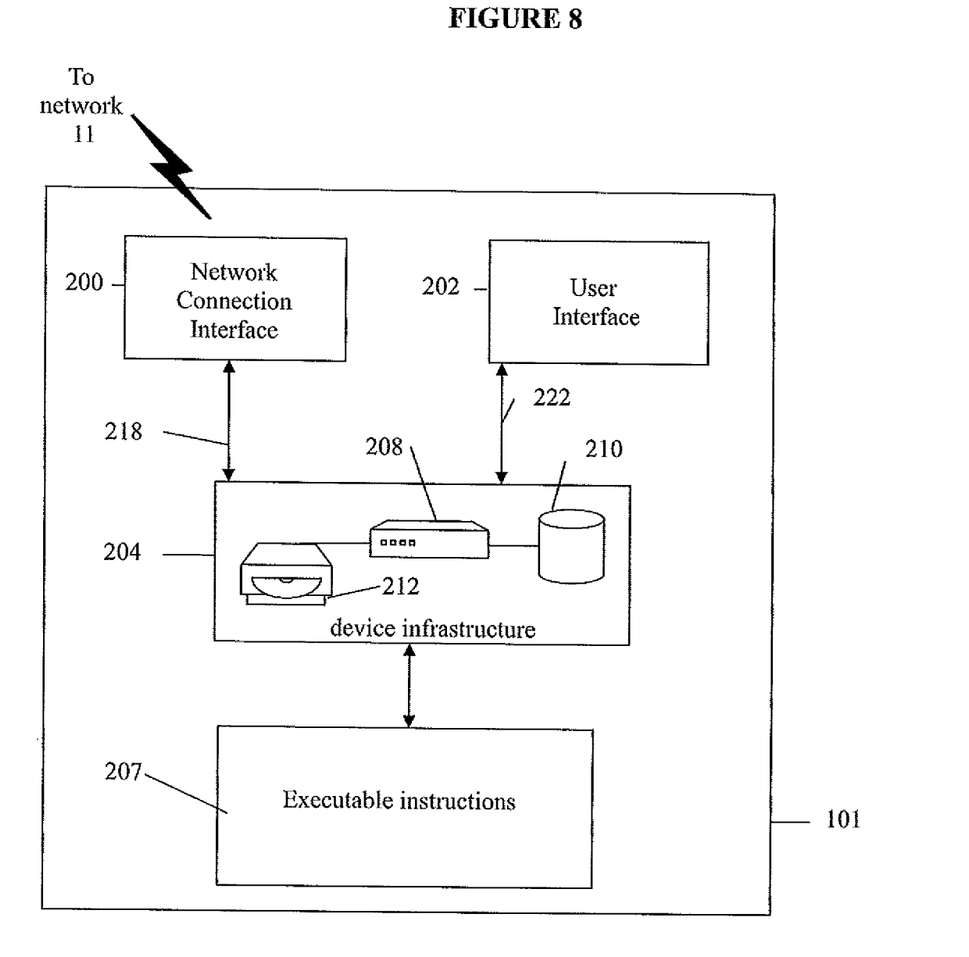
FIG. 8 illustrates a processing unit comprising computing devices in an embodiment of a system of FIG. 1.

Referring to FIG. 8, the signal processing unit 40 can be implemented on one or more respective computing device(s) 101. The devices 101 in general can include a network connection interface 200, such as a network interface card or a modem, coupled via connection 218 to a device infrastructure 204. The connection interface 200 is connectable during operation of the device(s) 101 to a network 11 (e.g. an intranet and/or an extranet such as the Internet) which enables the device(s) 101 to communicate with each other as appropriate. The network 11 can, for example, support the communication of the output signal (e.g. current/voltage signal) provided by the JVP device 10 to the signal processing device 40. The device(s) 101 may also have a user interface 202 coupled to the device infrastructure 204 by connection 222 to interact with a user. The user interface 202 can include one or more user input devices such as, but not limited to, a QWERTY keyboard, a keypad, a trackwheel, a stylus, a mouse, a microphone, a touch sensitive screen, and a user output device such as an LCD screen display and/or a speaker. Operation of the device(s) 101 is facilitated by the device infrastructure 204.

The device infrastructure 204 includes one or more computer processors 208 (e.g. a Digital Signal Processor) and can include an associated memory 210 (e.g. a random access memory). The computer processor 208 facilitates performance of the computing device 101 configured for the intended task through operation of the network interface 200, the user interface 202 and other application programs/hardware 207 of the computing device 101 by executing task-related instructions. These task-related instructions may be provided by an operating system and/or software applications 207 located in the memory 210, and/or by operability that is configured into the electronic/digital circuitry of the processor(s) 208 designed to perform the specific task(s). Further, it is recognized that the device infrastructure 204 may include a computer readable storage medium 212 coupled to the processor 208 for providing instructions to the processor 208. The computer readable medium 212 can include hardware and/or software such as, by way of example only, magnetic disks, magnetic tape, optically readable medium such as CD/DVD ROMS, and memory cards. In each case, the computer readable medium 212 may take the form of a small disk, floppy diskette, cassette, hard disk drive, solid-state memory card or RAM provided in the memory module 210. It should be noted that the above listed examples of computer readable media 212 may be used either alone or in combination. The device memory 210 and/or computer readable medium 212 may be used to store, for example, the desired output (e.g. pressure waveform) for use in processing of the signal received from the JVP device.

Further, it is recognized that the computing device(s) 101 may include executable applications 207 comprising code or machine readable instructions for implementing predetermined functions/operations including those of an operating system. The processor 208 as used herein is a configured device and/or set of machine-readable instructions for performing operations as described by example above. As used herein, the processor 208 may comprise any one or combination of, hardware, firmware, and/or software. The processor 208 acts upon information by manipulating, analyzing, modifying, converting or transmitting information for use by an executable procedure or an information device, and/or by routing the information with respect to an output device. The processor 208 may use or comprise the capabilities of a controller or microprocessor, for example, to communicate with the patient inclination controller 20, to provide information thereto, as above described, which permits the circuit controller 22 to appropriately activate the linear actuator 24 and adjust inclination of the back support 28. Accordingly, the functionality of the signal processing device 40, the JVP device and/or the patient inclination controller 20 may be implemented in hardware, software or a combination of both. Accordingly, the use of a processor 208 as a device and/or as a set of machine-readable instructions is hereafter referred to generically as a processor/module for the sake of simplicity. It will be understood that the computing device(s) 101 may be, for example, personal computers, personal digital assistants, mobile phones, and content players. Further, it is recognised that each server computing device 101, although depicted as a single computer system, may be implemented as a network of computer processors, as desired.

The invention claimed is:

1. A system configured to measure central venous pressure in a patient comprising:
   an optical device configured to measure jugular venous pressure, wherein the optical device comprises at least one light source adapted to emit light in the 400 nm to 1000 nm wavelength range; a plurality of adjacent photodetectors each adapted to receive light emitted by the at least one light source and transmit a current or voltage output signal;
   a processing unit which receives and processes the output signal from each of the plurality of photodetectors to calculate central venous pressure, wherein central venous pressure is determined by measuring the distance from the phlebostatic axis to the highest position on the jugular vein of the patient to yield the output signal, wherein the highest position is based on the output signal transmitted by a photodetector of the plurality of photodetectors which is adjacent to a photodetector of the plurality of photodetectors that transmits no significant output signal;
   a patient inclination controller comprising a control circuit in communication with the processing unit and a linear actuator; and
   a patient back support movable between a horizontal base position and a multitude of inclined positions by the linear actuator, or a vertical base position and a multitude of declined positions by the linear actuator,
   wherein the processing unit activates the control circuit of the patient inclination controller to activate the linear actuator to incline the patient back support from the horizontal base position when the output signal is transmitted by all of the plurality of photodetectors of the optical device or to decline the patient back support from the vertical base position when no significant output signal is transmitted by any of the plurality of photodetectors, to achieve a position of the back support that permits the optical device to detect the highest position along the jugular vein of the patient to yield the output signal.

2. The system of claim 1, wherein the plurality of adjacent photodetectors are adjacent along a length of about 1.5 to 10 cm of the device.

3. The system of claim 1, comprising at least one probe which facilitates delivery of light from the at least one light source to an external tissue site on the patient in the proximity of the jugular vein and receipt of light reflected from or transmitted through said patient site by the plurality of adjacent photodetectors.

4. The system as defined in claim 3, wherein said at least one light source and said plurality of adjacent photodetectors are embedded in said at least one probe.

5. The system as defined in claim 1, wherein said at least one light source is a plurality of light sources, and wherein each of said plurality of light sources emits light that is received by a corresponding photodetector of said plurality of adjacent photodetectors.

6. The system as defined in claim 1, wherein said processing unit comprises a microprocessor and a display unit.

\* \* \* \* \*